United States Patent [19]

Melvin, Jr. et al.

[11] 4,379,783

[45] Apr. 12, 1983

[54] TRIALKYLSILICON-CONTAINING PHENYLCYCLOALKANE ANALGESICS

[75] Inventors: Lawrence S. Melvin, Jr., Ledyard; Michael R. Johnson, Gales Ferry, both of Conn.

[73] Assignee: Pfizer Inc., New York, N.Y.

[21] Appl. No.: 381,591

[22] Filed: May 24, 1982

[51] Int. Cl.³ .................... A61K 31/695; C07F 7/08
[52] U.S. Cl. .................................. 424/184; 556/436; 556/440; 556/449
[58] Field of Search ................ 424/184; 556/436, 440, 556/449

[56] References Cited

U.S. PATENT DOCUMENTS 3,491,137  1/1970  Zaweski et al. ..................... 556/449
3,558,683  1/1971  Belsky et al. ....................... 424/184
3,586,705  1/1971  Owen et al. ........................ 556/449

Primary Examiner—Natalie Trousof
Assistant Examiner—P. M. Scott
Attorney, Agent, or Firm—Charles J. Knuth; Peter C. Richardson; Allen Bloom

[57] ABSTRACT

A compound of the formula

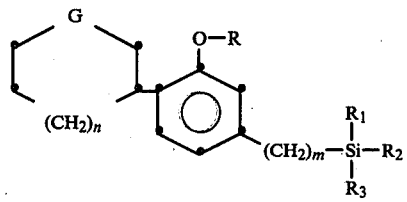

or a pharmaceutically acceptable salt thereof, wherein:
G is hydroxymethylene or carbonyl;
R is hydrogen or alkanoyl having from one to seven carbon atoms;
$R_1$ and $R_2$ are each methyl or ethyl;
$R_3$ is an alkyl of from five to seven carbon atoms;
m is 0 or 1; and
n is 1, 2 or 3.

A preferred compound is one in which m is zero, n is one or G is hydroxymethylene. Also preferred are compounds in which $R_1$ and $R_2$ are methyl. Additional preferred compounds include those where R is hydrogen or acetyl. A preferred compound is Z-3-(4'-(dimethyl-n-hexylsilyl)-2'-hydroxyphenyl)cyclohexanol.

The invention further comprises pharmaceutical compositions containing these compounds. In accordance with the present invention, these compounds when administered in an effective amount to mammals are useful as CNS agents including analgesics, tranquilizers, sedatives, anticonvulsants, antidiarrheals, antiemetics and antianxiety agents.

11 Claims, No Drawings

TRIALKYLSILICON-CONTAINING PHENYLCYCLOALKANE ANALGESICS

BACKGROUND OF THE INVENTION

This invention relates to compounds whose structure includes phenols, and alkyl esters thereof, having in the 2-position a cycloalkanol or cycloalkanone group as well as a sila-alkane substituent in the 5-position. These compounds are useful as CNS agents, especially as analgesics for treatment in mammals.

There is a continuing need for analgesic agents for the control of broad levels of pain and accompanied by a minimum of side-effects. The most commonly used agent, aspirin, is of no practical value for the control of severe pain and is known to exhibit various undesirable side-effects. Other analgesics such as d-propoxyphene, codeine and morphine, possess addictive liability. It is therefore desirable to discover compounds having improved and potent analgesic properties.

SUMMARY OF THE INVENTION

The present invention comprises novel compounds of the formula

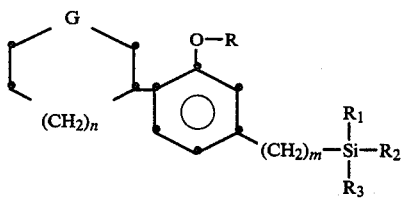

or pharmaceutically acceptable salts thereof, wherein:
G is hydroxymethylene or carbonyl;
R is hydrogen or alkanoyl having from one to seven carbon atoms;
$R_1$ and $R_2$ are each methyl or ethyl;
$R_3$ is an alkyl of from five to seven carbon atoms;
m is 0 or 1; and
n is 1, 2 or 3.

A preferred compound is one in which m is zero, n is one or G is hydroxymethylene. Also preferred are compounds in which $R_1$ and $R_2$ are methyl. Additional preferred compounds include those wherein R is hydrogen or acetyl. A preferred compound is Z-3-(4'-(dimethyl-n-hexylsilyl)-2'-hydroxyphenyl)-cyclohexanol.

The invention further comprises pharmaceutical compositions containing these compounds. In accordance with the present invention, these compounds when administered in an effective amount to mammals are useful as CNS agents including analgesics, tranquilizers, sedatives, anticonvulsants, antidiarrheals, antiemetics and antianxiety agents.

DETAILED DESCRIPTION OF THE INVENTION

A convenient starting material for the synthesis of the compounds of the present invention wherein m is zero is m-bromophenol. The bromophenol hydroxyl is protected, for example, by reaction with benzyl chloride under basic conditions. Other phenol protective groups, such as lower alkyl ethers, for example methyl or ethyl, may also be employed. The resulting bromophenyl benzyl ether is known:

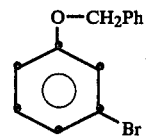

See Y.-H. Wu et al., *Journal of Medicinal and Pharmaceutical chemistry*, volume 5, pages 752-62 (1962).

The bromo ether is reacted with magnesium in an ether solvent such as tetrahydrofuran, 2-methyltetrahydrofuran or diethyl ether at reflux to form the Grignard reagent. The Grignard reagent is in turn reacted in situ with an appropriate dialkyldichlorosilane at about $-10°$ to 25° C., preferably 0° C., to form the corresponding dialkylchlorosilylphenol benzyl ether. The resulting chlorosilane is then reacted with an alkyl Grignard reagent in an ether such as tetrahydrofuran, 2-methyltetrahydrofuran or diethyl ether at $-10°$ to 25° C., preferably 0° C., so that the resulting trialkylsilane has the desired alkyl groups.

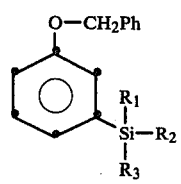

The benzyl protective group is now cleaved. A palladium on carbon catalyst can be employed in a hydrogenation reaction in an alcohol such as ethanol at 10°-40° C., preferably 25° C., to remove the benzyl group.

The resulting m-trialkylsilylphenol's hydroxyl group is protected by forming, for example, a methyl ether:

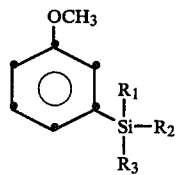

A convenient procedure is to employ an aprotic solvent under basic conditions, for example, dimethylformamide with sodium hydride or acetone with potassium carbonate, to form the phenolate at $-10°$ to 25° C., preferably 0° C. The phenolate is reacted in situ at 10° to 40° C., preferably 25° C., with an alkylating agent such as dimethylsulfate or methyl iodide.

An alternate procedure to obtain the m-trialkylsilylanisole is to begin with m-bromoanisole. The Grignard reagent is formed in an ether solvent such as tetrahydrofuran, 2-methyltetrahydrofuran or diethyl ether at reflux and reacted with a dialkyldichlorosilane in situ at $-10°$ to 25° C., preferably 0° C., to form the corresponding m-dialkylchlorosilylanisole which is in turn reacted with the appropriate alkyl Grignard reagent in an ether solvent such as tetrahydrofuran, 2-methyltetrahydrofuran or diethyl ether at $-10°$ to 25° C., preferably 0° C., to form the m-trialkylsilylanisole.

The m-trialkylsilylanisole is reacted with the appropriate six, seven or eight numbered ring alpha, beta-unsaturated cycloalkanone to obtain the desired cycloalkanone trialkylsilyl anisole:

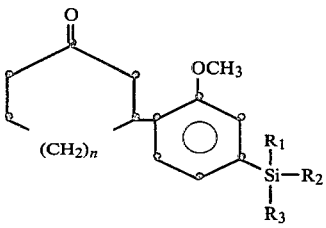

wherein n is 1, 2 or 3. Compounds wherein n is one are preferred. These addition compounds can be obtained by reacting the trialkylsilylanisole with an alkyl-lithium in the presence of a chelating agent such as N,N,N,N-tetraethylenediamine at 10°–50°, preferably 25° C. followed by in situ reaction with a 1-alkyne copper-lithium reagent at −78° to −20° C., preferably −78° C., in an ether solvent such as tetrahydrofuran or 2-methyltetrahydrofuran. The intermediate copper-lithium anisole is reacted in situ with the alpha, beta-unsaturated cycloalkanone at −78° to −20° C., preferably −78° C.

The ketone can be reduced, if desired, using any convenient reducing agent such as sodium borohydride in alcoholic solvents such as methanol at −78° to −20° C., preferably −78° C.

The methyl ether group protecting the phenolic hydroxyl can be removed with a lithium alkyl mercaptide such as lithium n-propyl mercaptide in a polar, aprotic solvent such as hexamethylphosphoramide at about 50°–150° C., preferably 105° C.

If the ketone is not to be reduced, a ketal can be formed to protect the carbonyl group during removal of the methyl ether protecting group. One method of ketalization is reacting the ketone with an alkyl alcohol, especially one having one to four carbon atoms, in the presence of an acid such as sulfuric acid, p-toluenesulfonic acid or hydrogen chloride under conditions which remove the by-product water. In one method an alcohol having a boiling point higher than water is employed and the water is distilled off. Alternatively, if an azeotrope forms between water and the alcohol, the azeotrope can be distilled off. Cyclic ketals can be formed using diols such as ethylene glycol as the starting alcohol. Another reaction method for ketal formation is the reaction of the ketone with an orthoformate ester in an alcohol solution where the alcohol corresponds to the alkoxy moiety of the orthoformate ester. Trimethyl orthoformate and methanol can be employed in this reaction with concentrated sulfuric acid, anhydrous hydrogen chloride or ammonium chloride as the acid catalyst.

When the ketal is no longer desired, it can be converted back to the ketone by known procedures such as treatment with aqueous acid at 10°–50° C., preferably 25° C.

Alternatively, the cycloalkanol can be reoxidized to the ketone following removal of the methyl ether protecting group using an oxidizing agent such as aqueous potassium dichromate or chromium trioxide in glacial acetic acid or pyridine.

If the phenolic ester of an alkyl carboylic acid having 1–7 carbon atoms is desired, the phenol can be reacted with the corresponding acid anhydride with an acid acceptor such as 4-N,N-dimethylaminopyridine at −10° to 25° C., preferably 0° C., or with the corresponding acid chloride in the presence of an acid acceptor such as sodium or potassium carbonate in an nonnucleophilic solvent to obtain the desired phenolic ester product. The preferred alkanoyl has two carbon atoms, i.e., acetyl.

If the desired compound has a methylene group interposed between the phenyl and trialkylsilyl groups an appropriate starting material is:

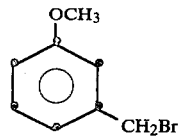

which can be prepared from 3-methoxybenzyl alcohol (W. Q. Beard, Jr., et al., *Journal of Organic Chemistry*, Volume 26, page 2310 (1961)). Other phenol hydroxyl protecting groups such as benzyl ether which was employed for compounds without an interposed methylene group can also be used in the present case. The same general synthetic sequences employed for m-bromoanisole as the starting material can be employed for m-bromomethylanisole. Of course other halogen-substituted anisoles can also serve as starting materials.

The alkyl groups about the silicon are $R_1$ and $R_2$ each being independently methyl and ethyl, $R_1$ and $R_2$ both being methyl is preferred; and $R_3$ being alkyl having five to seven carbon atoms, preferably six.

When R is hydrogen, phenolic cationic salts can be formed. Pharmaceutically acceptable cations can include lithium, sodium, potassium, calcium, magnesium and the like.

The analgesic properties of the compounds of this invention are determined by tests using nociceptive stimuli.

Test Using Thermal Nociceptive Stimuli

Mouse Hot Plate Analgesic Testing

The method used is modified after Woolfe and MacDonald, *J. Pharmacol. Exp. Ther.*, 80, 300–307 (1944). A controlled heat stimulus is applied to the feet of mice on a ⅛ inch thick aluminum plate. A 250 watt reflector infrared heat lamp is placed under the bottom of the aluminum plate. A thermal regulator, connected to thermistors on the place surface, programs the heat lamp to maintain a constant temperature of 57° C. Each mouse is dropped into a glass cylinder (6½ inch diameter) resting on the hot plate, and timing is begun when the animal's feet touch the plate. The mouse is observed at 0.5 and 2 hours after treatment with the test compound for the first "flicking" movements of one or both hind feet, or until 10 seconds elapse without such movements. Morphine has an $MPE_{50}=4$–5.6 mg./kg.(s.c.).

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with an intraperitoneal injection of phenylbenzoquinone, an irritant known to produce abdominal contractions. The mice are observed for 5 minutes for the presence or absence of writhing starting 5 minutes after the injection of the irritant. MPE$_{50}$'s of the drug pretreatments in blocking writhing are ascertained.

Test Using Pressure Nociceptive Stimuli

Effect on the Haffner Tail Pinch Procedure

A modification of the procedure of Haffner, *Experimentelle Prufung Schmerzstillender. Deutch Med. Wschr.*, 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5 inch "bulldog" clamp is clamped onto the root of the rat's tail. The endpoint at each trial is clear attacking and biting behavior directed toward the offending stimulus, with the latency for attack recorded in seconds. The clamp is removed in 30 seconds if attacking has not yet occurred, and the latency of response is recorded as 30 seconds. Morphine is active at 17.8 mg./kg.(i.p.).

Test Using Electrical Nociceptive Stimuli

The "Flinch-Jump" Test

A modification of the flinch-jump procedure of Tenen, *Psychopharmacologia*, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30 second intervals. These intensities are 0.26, 0.39, 0.52, 0.78, 1.05, 1.31, 1.58, 1.86, 2.13, 2.42, 2.72 and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (%MPE). The %MPE of each group is statistically compared to the %MPE of the standard and the predrug control values. The %MPE is calculated as follows:

$$\% MPE = \frac{\text{test time} - \text{control time}}{\text{cutoff time} - \text{control time}} \times 100$$

The compounds of this invention, when used as analgesics via oral or parenteral administration, are conveniently administered in composition form. Such compositions include a pharmaceutical carrier selected on the basis of the chosen route of administration and standard pharmaceutical practices. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixers which may contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in human adults weighing about 68 kg will range from about 0.1 to about 750 mg. per day in single or divided doses. In many instances, it is not necessary to exceed 100 mg. daily. The favored oral dosage range is from about 1.0 to about 300 mg./day; the preferred dose is from about 1.0 to about 50 mg./day. The favored parenteral dose is from about 0.1 to about 100 mg./day; the preferred range from about 0.1 to about 20 mg./day.

This invention also provides pharmaceutical compositions, including unit dosage forms, valuable for the use of the herein described compounds as analgesics and other utilities disclosed herein. The dosage form can be given in single or multiple doses, as previously noted to achieve the daily dosage effective for a particular utility.

The compounds described herein can be formulated for administration in solid or liquid form for oral or in liquid form for parenteral administration. For example, capsules containing drugs of this invention can be prepared by mixing one part by weight of drug with nine parts of excipient such as starch or milk sugar and then loading the mixture into telescoping gelatin capsules such that each capsule contains 100 parts of the mixture. Tablets containing said compounds can be prepared, for example, by compounding suitable mixtures of drug and standard ingredients used in preparing tablets, such as starch, binders and lubricants, such that each tablet contains from about 0.10 mg. of drug per tablet.

Suspensions and solutions of these drugs are often prepared just prior to use in order to avoid problems of stability of the suspensions or solution (e.g. precipitation) of the drug upon storage. Compositions suitable for such are generally dry solid compositions which are reconstituted for injectable administration.

The tranquilizer activity of the compounds of this invention is determined by orally administering them to rats at doses of from about 0.01 to about 50 mg./kg. of body weight and observing the subsequent decreases in spontaneous motor activity. The daily dosage range in mammals is from about 0.01 to about 100 mg.

Anticonvulsant activity is determined by subcutaneously administering the test compound to male Swiss mice (Charles River) weighing 14–24 g. in a suitable vehicle. The mice are used in groups of five. The day before use, the mice are fasted overnight but watered ad lib. Treatments are given at volumes of 10 ml. per kg. via a 25 gauge hypodermic needle. Subjects are treated with the test compound followed one hour later by challenge electroconvulsive shock, 50 mA. at 60 Hz. administered transcorneally. Controls are simultaneously run in which the mice are given only the vehicle as control treatment. The electroconvulsive shock treatment produces tonic extensor convulsions in all control mice with a latency of 1.5–3 seconds. Protection is recorded when a mouse exhibits no tonic extensor convulsions for 10 seconds after administration of electroconvulsive shock.

Antianxiety activity is determined in a manner similar to that for evaluating anticonvulsant activity except that the challenge convulsant is pentylenetetrazole, 120 mg./kg. administered intraperitoneally. This treatment produces chronic convulsions in less than one minute in over 95% of control mice treated. Protection is recorded when the latency to convulse is delayed at least 2-fold by a drug pretreatment.

Sedative/depressant activity is determined by treating groups of six mice subcutaneously with various doses of test agents. At 30 and 60 minutes post treatment, the mice are placed on a rotorod for one minute and evaluated for their performance on the rotorod. Inability of the mice to ride the rotorod is taken as evidence of sedative/depressant activity.

The antiemetic properties of the compounds of the present invention can be determined in unanesthetized cats according to the procedure described in *Proceedings of the Society of Experimental Biology and Medicine*, volume 160, pages 437–40 (1979). The antidiarrheal utility can be determined by a modification of the procedure of Neimgeers et al. *Modern Pharmacology-toxicology*, van Bever et al. Eds., volume 7, pages 68–73 (1976). In general the dosage levels and routes of administration for use of these compounds as tranquilizers, anticonvulsants, sedatives or antianxiety, antiemetic or antidiarrheal agents parallels those with respect to their use as analgesic agents.

The present invention will be illustrated by means of the following examples. It is to be understood, however, that the invention is not meant to be limited by the details described therein.

Infrared (IR) spectra were measured in chloroform ($CHCl_3$) solutions and diagnostic absorption bands are reported in wave numbers ($cm^{-1}$). Proton nuclear magnetic resonance spectra (PMR) were measured at 60 MHz for solutions in deutero-chloroform and peak positions are expressed in parts per million downfield from tetramethylsilane. The peak shapes are denoted as follows: s, singlet; d, doublet; t, triplet; q, quartet; m, multiplet; b, broad. Mass spectra (MS) or high resolution mass spectra (HRMS) are reported as positive ion mass per electron charge (m/e) with the parent ion denoted $M^+$.

EXAMPLE 1

Z-3-(4'-(Dimethyl-n-hexylsilyl)-2'-hydroxyphenyl)cyclohexanol

To a degassed, solution, of 150 mg (0.432 mmole) of Z-3-(4'-(dimethyl-n-hexylsilyl)-2'-methoxyphenyl)-cyclohexanol in hexamethylphosphoramide at 25° C. was added 2.16 ml of 1 M lithium n-propylmercaptide in hexamethylphosphoramide. The reaction mixture was kept at 105° C. for 1 hour and then added to 100 ml of aqueous pH 7 buffer at 25° C. The quenched reaction mixture was extracted with 300 ml diethyl ether. The ether extract was washed three times with 200 ml water, washed once with 200 ml saturated aqueous sodium chloride, dried over anhydrous magnesium sulfate and evaporated to an oil. The oil was purified by preparative layer chromatography on silica gel plates (2 mm×20 cm×20 cm) eluted with 50% diethyl ether-hexane to give, after crystallization in hexane, 100 mg (69%) of the title compound, m.p. 93°–95° C.

PMR: 0.22 (s, $Si(CH_3)_2$), 3.0 (bm, CH), 3.8 (bm, CH) and 6.8–7.2 (m, aromatic H) ppm.

The title compound was tested using suppression of phenylbenzoquinone irritant-induced writhing as previously described. The $MPE_{50}$ was 2.2 mg/kg if the title compound was administered subcutaneously and 2.4 mg/kg, if administered orally.

Example 2

3-(4'-(Dimethyl-n-hexylsilyl)-2'-hydroxyphenyl)-cyclohexanone

The same procedures and materials can be employed as in Example 1 except the starting material is 3-(4'-(dimethyl-n-hexylsilyl)-2'-methoxyphenyl)cyclohexanone rather than Z-3-(4-dimethyl-n-hexylsilyl-2-methoxyphenyl)cyclohexanol.

Example 3

Z-3-(4'-(Dimethyl-n-hexylsilylmethyl)-2'-hydroxyphenyl)-cyclohexanol

The same procedures and materials as in Example 1 can be employed except the starting material is Z-3-(4'-dimethyl-n-hexylsilylmethyl)-2'-methoxyphenyl)-cyclohexanol rather than Z-3-(4'-(dimethyl-n-hexyl)-silyl)-2'-methoxyphenyl)cyclohexanol.

Example 4

Z-3-(4'-(Dimethyl-n-hexylsilyl)-2'-acetoxyphenyl)-cyclohexanol

To a 0° solution of 2.0 g of Z-3-(4'-(dimethyl-n-hexylsilyl)-2'-hydroxyphenyl)cyclohexanol in 10 ml of dichloromethane is added 0.73 g. of 4-N,N-dimethylaminopyridine and 0.56 ml of acetic anhydride. The reaction is stirred 2 hrs. at 0° and then added to 200 ml diethyl ether and 50 ml 1 N hydrochloric acid. The organic phase is washed with 100 ml saturated aqueous sodium bicarbonate, dried over anhydrous magnesium sulfate and evaporated to yield the title compound as an oil. Purification, if needed, can be achieved via recrystallization from hexane-ether or column chromatography on silica gel eluted with diethyl ether-hexane.

PREPARATION A

1-Benzyloxy-3-(dimethyl-n-hexylsilyl)benzene

To a refluxing slurry of 3.6 g. (0.15 mole) of magnesium in 100 ml. tetrahydrofuran was slowly added a solution of 26.3 g. (0.1 mole) of 1-benzyloxy-3-bromobenzene in 100 ml. tetrahydrofuran. After addition the reaction was allowed to cool to 25° C. The resulting Grignard reagent was added over a 30 minute period to 64.5 g. (0.504 mole) of dichlorodimethylsilane at 0° C. The reaction mixture was allowed to warm to 25° C. and the excess dichlorodimethylsilane and tetrahydrofuran were removed in vacuo. The residual gel was dissolved in 100 ml. tetrahydrofuran and cooled to 0° C. To this 0° C. solution was added, over a 30 minute period, 80 ml. of 2 M n-hexylmagnesium bromide in diethyl ether and the reaction was then allowed to warm to 25° C. The reaction was quenched by addition to 1 liter saturated ammonium chloride and the quenched reaction mixture was extracted with 1 liter diethyl ether. The diethyl ether extract was washed twice with 1 liter water, dried over anhydrous magnesium sulfate and evaporated to an oil. This oil was purified by column chromatography on 500 g. silica gel eluted with 3% diethyl ether-hexane to yield 28.4 g. (87%) of the title compound as an oil.

PMR: 0.27 (s, $Si(CH_3)_2$), 0.88 (m, $SiCH_2$ and $CH_3$), 1.28 (m, $(CH_2)_4$), 5.08 (s, $CH_2$) and 6.9–7.4 (m, aromatic H) ppm.

IR: ($CHCl_3$) 1575 $cm^{-1}$.

MS: m/e 326 ($M^+$), 311, 241, 235, 227, 151, 135, 122 and 91.

PREPARATION B

3-(Dimethyl-n-hexylsilyl)phenol

A mixture of 34.8 g. (0.107 mole) of 1-benzyloxy-3-(dimethyl-hexylsilyl)benzene, 2.0 g. of a 1:1 mixture by weight to volume of 5% by weight palladium on carbon and water, and 100 ml. ethanol was stirred under 1 atm. hydrogen at 25° C. until hydrogen uptake ceased (after an uptake of 2.5 liters). The reaction was filtered through Supercel with ethanol and the filtrate evaporated to a quantitative yield of the title compound as an oil.

PMR: 0.23 (s, Si(CH$_3$)$_2$, 0.89 (m, SiCH$_2$ and CH$_2$), 1.30 (m, (CH$_2$)$_4$), 4.89 (bs, OH) and 6.75–7.38 (m, aromatic H) ppm.

IR: (CHCl$_3$) 3571, 3279 and 1580 cm$^{-1}$.

MS: m/e 236 (M+), 221, 209, 200, 181, 151 and 137.

PREPARATION C

3-(Dimethyl-n-hexylsilyl)-1-methoxybenzene

To a 0° C. slurry of 3.98 g. (0.166 mole) of sodium hydride in 50 ml. dimethylformamide was slowly added a solution of 26.1 g. (0.111 mole) of 3-(dimethyl-n-hexylsilyl)phenol in 50 ml. dimethylformamide. Following addition, the reaction mixture was stirred 1 hr at 25° C. and cooled to 0° C. To the cooled reaction mixture, 20.9 g. (0.166 mole) of dimethyl sulfate was slowly added. Following addition, the reaction was stirred for 2 hr at 25° C. and then added to 200 ml. water. The quenched reaction mixture was extracted with three 100 ml. portions of hexane. The hexane extract was dried over anhydrous magnesium sulfate and evaporated to an oil. This oil was purified by column chromatography on 500 g. of silica gel eluted with 1% diethyl ether hexane to yield 14.8 g. (53%) of the title compound as an oil.

PMR: 0.26 (s, Si(CH$_3$)$_2$), 0.78 (m, CH$_2$ and CH$_3$), 1.20 (m, (CH$_2$)$_4$), 3.67 (s, OCH$_3$) and 6.6–7.3 (m, aromatic H) ppm.

IR: (CHCl$_3$) 1600 and 1574 cm$^{-1}$.

HRMS: m/e 250.1776 (M+, calcd for C$_{15}$H$_{26}$OSi: 250.1746), 235, 166, 165 and 151.

PREPARATION D

3-(4'-(Dimethyl-n-hexylsilyl)-2'-methoxyphenyl)cyclohexanone

To a 25° C. solution of 2.00 g. (8.0 mmole) of 3-(dimethyl-n-hexylsilyl)-1-methoxybenzene and 1.32 ml. (8.8 mmole) of N,N,N',N'-tetramethylethylenediamine in 8 ml. diethyl ether was added 3.2 ml. of 2.5 M n-butyllithium in hexane. The reaction solution was heated at reflux for 1 hr and then cooled to −78° C. To the −78° C. solution was added 9.68 mmole of 1-hexynyl copper lithium in 20 ml. tetrahydrofuran. The resultant yellow mixture was stirred 5 minute at −78° C. and then 768 mg. (8.0 mmole) of cyclohex-2-en-1-one was slowly added. The reaction mixture was stirred for 5 minute longer at −78° C. and then warmed to −20° C. and stirred for 5 minute. The reaction mixture was added to 500 ml. saturated aqueous ammonium chloride adjusted to pH 9 with saturated aqueous ammonium hydroxide. The quenched reaction was extracted five times with 500 ml. diethyl ether. The diethyl ether extracts were dried over magnesium sulfate and evaporated to an oil. The crude oil was purified by column chromatography on 200 g. of silica gel eluted with 10% diethyl ether-hexane to yield 1.0 g. (36%) of the title compound as an oil.

PMR: 0.22 (s, Si(CH$_3$)$_2$), 3.80 (s, OCH$_3$) and 6.9–7.2 (m, aromatic H).

HRMS: m/e 346.2342 (M+, calcd for C$_{21}$H$_{34}$O$_2$Si: 346.2319), 261 and 247.

PREPARATION E

Z-3-(4'-(Dimethyl-n-hexylsilyl)-2'-methoxyphenyl)cyclohexanol

To a −78° C. solution of 1.0 g. (2.8 mmole) of 3-(4-dimethyl-n-hexylsilyl-2-methoxyphenyl)cyclohexanone in 10 ml. methanol and 2 ml. tetrahydrofuran was added 1.0 g. (26.3 mmole) of sodium borohydride. The reaction was stirred 30 minute at −78° C. and then added to 500 ml. aqueous saturated sodium chloride and 350 ml. diethyl ether. The diethyl ether portion was dried over anhydrous magnesium sulfate and evaporated to an oil. The crude oil was purified by column chromatography on 200 g. of silica gel eluted with 30–50% diethyl ether-hexane to yield in order of elution 35 mg. (3%) of E-3-(4-dimethyl-n-hexylsilyl-2-methoxyphenyl)cyclohexanol and 296 mg. (30%) of the title compound as oils.

Title compound PMR: 0.23 (s, Si(CH$_3$)$_2$), 3.75 (bm, CH), 3.80 (s, OCH$_3$) and 6.9–7.3 (m, aromatic H) ppm.

PREPARATION F

3-(Dimethyl-n-hexylsilyl)methyl-1-methoxysilane

The same materials and procedures as in Preparation A can be employed except the starting material is 3-bromo-methoxybenzene rather than 1-benzyloxy-3-bromobenzene.

PREPARATION G

3-(4'-(Dimethyl-n-hexylsilyl)methyl)-2'-methoxyphenyl)cyclohexanone

The same materials and procedures as in Preparation D can be employed except the starting material is 3-(dimethyl-n-hexylsilyl)methyl-1-methoxybenzene rather than 3-(dimethyl-n-hexylsilyl)-1-methoxybenzene.

PREPARATION H

Z-3-(4'-Dimethyl-n-hexylsilyl)methyl)-2'-methoxyphenyl)cyclohexanol

The same procedures and materials as in Preparation E can be employed except the starting material is 3-(4'-(dimethyl-n-hexylsilyl)methyl)-2'-methoxy-phenyl)cyclohexanone rather than 3-(4'-(dimethyl-n-hexyl)-silyl-2'-methoxyphenyl)cyclohexanone.

We claim:

1. A compound having the formula

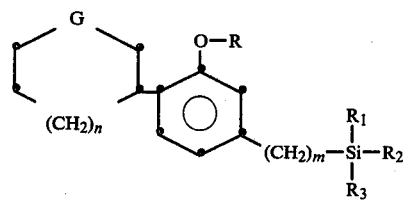

or a pharmaceutically acceptable salt thereof, wherein:
G is hydroxymethylene or carbonyl;
R is hydrogen or alkanoyl having from one to seven carbon atoms;

$R_1$ and $R_2$ are methyl or ethyl;
$R_3$ is an alkyl of from five to seven carbon atoms;
m is 0 or 1; and
n is 1, 2 or 3.

2. A compound according to claim 1 wherein m is zero.

3. A compound according to claim 1 wherein n is 1.

4. A compound according to claim 1 wherein G is hydroxymethyl.

5. A compound according to claim 1 wherein $R_1$ and $R_2$ are methyl.

6. A compound according to claim 1 wherein R is hydrogen.

7. A compound according to claim 1 wherein R is acetyl.

8. A compound according to claim 1 wherein m is zero, n is 1, $R_1$ and $R_2$ are methyl, R is hydrogen and G is hydroxymethylene.

9. A compound according to claim 1 or claim 8 wherein $R_3$ is n-hexyl.

10. A pharmaceutical composition comprising a pharmaceutically acceptable carrier or diluent and an analgesic, tranquilizer, sedative, antianxiety, anticonvulsant, antidiarrheal or antiemetic effective amount of a compound of claim 1 or claim 2.

11. A method for producing analgesia in a mammal which comprises administering thereto an analgesia-producing quantity of a compound of claim 1 or claim 2.

* * * * *